US012693437B2

(12) United States Patent
Vija et al.

(10) Patent No.: US 12,693,437 B2
(45) Date of Patent: Jul. 28, 2026

(54) EDGE ARRANGEMENT FOR TILEABLE PIXELATED EMISSION SENSOR

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 267 days.

(21) Appl. No.: 18/683,829

(22) PCT Filed: Nov. 16, 2021

(86) PCT No.: PCT/US2021/072427

§ 371 (c)(1),
(2) Date: Feb. 15, 2024

(87) PCT Pub. No.: WO2023/091162

PCT Pub. Date: May 25, 2023

(65) Prior Publication Data

US 2024/0361477 A1     Oct. 31, 2024

(51) Int. Cl.
| | |
|---|---|
| *G01T 1/24* | (2006.01) |
| *A61B 6/42* | (2024.01) |
| *G01T 1/20* | (2006.01) |
| *H10F 39/00* | (2025.01) |
| *H10F 39/18* | (2025.01) |

(52) U.S. Cl.
CPC ............ *G01T 1/243* (2013.01); *A61B 6/4233* (2013.01); *A61B 6/4258* (2013.01); *A61B 6/4266* (2013.01); *G01T 1/20182* (2020.05); *H10F 39/022* (2025.01); *H10F 39/1892* (2025.01)

(58) Field of Classification Search
CPC ............................ G01T 1/20182; G01T 1/243
See application file for complete search history.

(56) References Cited

U.S. PATENT DOCUMENTS

| | | | |
|---|---|---|---|
| 6,510,195 B1 | 1/2003 | Iwanczyk et al. | |
| 7,170,049 B2 | 1/2007 | Iwanczyk et al. | |
| 7,339,176 B2 | 3/2008 | El-Hanany et al. | |
| 9,681,847 B2 | 6/2017 | Mis | |

(Continued)

FOREIGN PATENT DOCUMENTS

| | | |
|---|---|---|
| CN | 103296036 | 9/2013 |
| DE | 102012202500 | 8/2013 |

(Continued)

OTHER PUBLICATIONS

International Search Report for corresponding application No. PCT/US2021/072427, dated Mar. 16, 2022.

*Primary Examiner* — Casey Bryant

(57) ABSTRACT

For larger FOV in a gamma camera, multiple solid-state detectors are tiled. The edge pixels of the pixelated detectors are smaller than interior pixels so that the pitch of the pixels or anodes is constant across the tiled detectors. The constant pitch occurs where pairs of edge pixels combined from different detectors contribute the pitch or area of an interior pixel. As a result of this optimized edge pixel pairing and corresponding regular pitch across the tiles, the spectral and other performance is less degraded.

10 Claims, 5 Drawing Sheets

(56) References Cited

U.S. PATENT DOCUMENTS

| | | | |
|---|---|---|---|
| 2002/0089595 A1 | 7/2002 | Orava et al. | |
| 2005/0167606 A1 | 8/2005 | Harrison et al. | |
| 2011/0218432 A1 | 9/2011 | Tumer | |
| 2014/0138543 A1 | 5/2014 | LaVeigne | |
| 2016/0104696 A1 | 4/2016 | LaVeigne | |
| 2016/0344943 A1* | 11/2016 | Lee ........................ | H04N 5/265 |
| 2017/0322319 A1 | 11/2017 | Iniewski et al. | |
| 2021/0290189 A1 | 9/2021 | Vlja et al. | |

FOREIGN PATENT DOCUMENTS

| | | | | |
|---|---|---|---|---|
| DE | 102012202500 A1 * | 8/2013 | ........... | A61B 6/4233 |
| JP | H085746 | 1/1996 | | |
| JP | 2002236179 | 8/2002 | | |
| JP | 2002236179 A * | 8/2002 | | |
| JP | 2008506945 | 9/2013 | | |
| WO | WO-2019201544 A1 * | 10/2019 | ........... | H01J 37/244 |
| WO | 2021071549 A1 | 4/2021 | | |

* cited by examiner

802     Tiling Pixelated Detectors

804     Aligning Edge Pixels to Maintain Pitch

EDGE ARRANGEMENT FOR TILEABLE PIXELATED EMISSION SENSOR

BACKGROUND

The present embodiments relate to semiconductor detectors for single photon emission computed tomography (SPECT), photon emission tomography (PET), or another imager using a gamma camera. Large field of view (FOV) gamma cameras tile multiple two-dimensional (2D) solid-state detectors with pixelated anodes. Most designs are square-shaped. Each detector is a 2D array of pixels where each pixel or anode has the same size and shape as the others. The steering grid electrode in designs may be as large as a pixel size, reducing the percentage of the sensor surface area that is sensitive to radiation detection (i.e., reducing the fill factor or area for sensing).

The edge pixels are larger than or same size as other pixels, reducing detection area, increasing gaps, and adding difficulty for use in large FOV gamma cameras. The pixels on the edges have lower performance as compared to interior pixels. Degraded spectral performance near the edges (or readout electrodes) of pixelated solid-state sensors is due to increased defects by mechanically induced stress during manufacturing operations (i.e., cutting, polishing, passivation, and other processes). The electric field bends outside the sensor volume near the edges (dipole effect), steering electrons towards the edges of the sensor for interactions happening between the center and cathode surface, and steering holes towards the edges of the sensor for interactions happening between the center and anode surface. This steering effect contributes to degraded spectral performance near the edges. The steering-grid also increases the capacitance of the edge electrodes, so also contributes to degraded performance at the edges. Finally, dark current (noise) at the edge electrodes may be slightly higher, thus degrading the performance at the edge pixels.

A guard ring may be provided around each 2D solid-state detector, resulting in further separation between pixels of different detectors when tiled. The non-uniform spacing when tiled provides poor registration to collimators.

SUMMARY

By way of introduction, the preferred embodiments described below include methods, systems, and detectors for tileable gamma camera. For larger FOV, multiple solid-state detectors are tiled. The edge pixels of the pixelated detectors are smaller than interior pixels so that the pitch of the pixels or anodes is constant across the tiled detectors. The constant pitch occurs where pairs of edge pixels combined from different detectors contribute the pitch or area of an interior pixel. As a result of this optimized edge pixel pairing and corresponding regular pitch across the tiles, the spectral and other performance is less degraded.

In a first aspect, a detector system includes a first detector having a plurality of first pixelated detector cells including first interior detector cells and first edge detector cells on a first edge of the first detector and includes a second detector having a plurality of second pixelated detector cells including second interior detector cells and second edge detector cells on a second edge of the second detector. The first detector is tiled with the second detector such that the second detector is positioned adjacent to the first detector where the first edge is by the second edge. The first edge detector cells have a first lesser area than the first interior detector cells, and the second edge detector cells have a second lesser area than the second interior detector cells. The first and second lesser areas are sized such that pairs of the first and second edge detector cells form combination cells so that a pitch of the first and second pixelated detectors cells across the first and second detectors is constant.

Various shapes may be used. For example, the first and second interior detector cells and the combination cells are square where the first and second edge detector cells are rectangular. As another example, the first and second interior detector cells and the combination cells are triangular where some of the first and second edge detector cells being triangular and others of the first and second edge detector cells are trapezoidal. In another example, the first and second interior detector cells and the combination cells are hexagonal where the first and second edge detector cells are five sided.

In one embodiment, the first and second lesser areas are substantially equal. In another embodiment, the first and second lesser areas are about ½ of areas of the first and second interior detector cells, respectively.

No gap is provided between the first and second detectors. In other embodiments, a gap less than the pitch between the first and second detectors is provided. The first and second lesser areas are less than ½ of areas of the first and second interior detector cells, respectively, such that the pitch is constant even with the gap.

In one embodiment, the first and second detectors comprise room temperature semiconductor detectors. Other solid-state detectors may be used.

In an embodiment, the first and second detectors have a same shape, and the first and second interior detector cells have the same shape.

In another embodiment, the first and second pixelated detector cells include corner edge detector cells being ½ or less of the first and second lesser areas.

In a second aspect, a solid-state sensor is provided. A tiled arrangement of semiconductor wafers is provided. The semiconductor wafers each have a shape of a detection face and each have detection cells with the shape. The detection cells on edges of abutting different ones of the semiconductor wafers are shaped so that pairs of the detection cells on the edges from the abutting different ones of the semiconductor wafers form the shape.

In one embodiment, the shape is square. The detection cells on the edges from the abutting different ones of the semiconductor wafers are rectangular and ½ or less of an area than detection cells not on the edges. In another embodiment, the shape is hexagonal. The detection cells on the edges from the abutting different ones of the semiconductor wafers are five sided and ½ or less of an area than detection cells not on the edges.

In other embodiments, a gap is between the abutting different ones of the semiconductor wafers. The detection cells on the edges have less than ½ an area of the detection cells not on the edges.

As another embodiment, a pitch of the detection cells across the tiled arrangement is fixed where the pairs of the detection cells on the edges act as a single cell for the pitch.

In a third aspect, a method is provided for forming a gamma camera. Solid-state detectors are tiled in an arrangement with a same pitch of pixels across the tiled solid-state detectors. The solid-state detectors are aligned as part of the tiling. The aligning pairs pixels on edges of different ones of the solid-state detectors to have a same size and shape as pixels not on the edge so that each of the paired pixels provide the same pitch as each of the pixels not on the edge.

In one embodiment, the solid-state detectors are square. The pixels on the edges are rectangular and each has ½ or less of an area of the pixels not on the edge for alignment. In another embodiment, the solid-state detectors are hexagonal. The pixels on the edges are five sided and each has ½ or less of an area of the pixels not on the edge for alignment.

In an embodiment, the solid-state detectors are placed adjacent each other with a gap separating them. The pixels on the edge so that the paired pixels on the edge plus part of the gap are aligned to provide the pitch.

In another embodiment, the aligning is performed so that the paired pixels on the edge have a same shape as the pixels not on the edge and of the solid-state detectors.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An optimized sensor edge anode pattern improves edge pixels spectral performance and keeps symmetry across multiple axes of symmetry across multiple sensors when operating side-by-side. Tiling solid-state detectors in 2D space uses edge anode patterns to maintain a fixed pitch between pixels across the multiple sensors, improving edge pixels spectral performance. The edge pixels are reduced in area so that pairs of edge pixels from different detectors combine in area to maintain the pitch across detectors. The detectors and corresponding pixels (e.g., anode electrodes) have the same shape, such as triangular, square, or hexagonal, with constant pitch along any dimension across the detectors.

This configuration may improve overall system response with better uniformity when tiling multiple sensors side-by-side, facilitating detection and correction schemes. The capacitance of the edge and corner pixels is reduced, thus improving the spectral performance and sub-pixel positioning at the edges. Improved spectral performance at edges, better multi-sensor symmetry, reduction of the relative area of edge pixels to the total area of the detector (i.e., improved the fill factor), reduction of the capacitance of the edge pixels/corner (e.g., due to smaller pixels), and/or higher signal-to-noise ratio by sub-pixel positioning at the edges may be provided. The relative area of edge pixels to the total area of the detector is reduced by having smaller edge pixels, thus improving the fill factor.

The fixed pitch may provide for better registration between a collimator and detector pixels 1-1. Symmetry across multiple sensors tiled in 2D space is desirable in imaging with a multichannel collimator. Other collimation or collimation-less schemes also benefit from equally spaced pixels with improved edge pixel spectral performance.

The tileable sensors are used for emission imaging, such as forming a gamma camera. The gamma camera is used for SPECT, PET, or another instrument design. SPECT provides image formation using classical multichannel collimation. The SPECT example will be used herein. The sensors are used in any image formation suitable to gamma ray imaging, tomographic or not. The gamma camera may be used for medical emission imaging or non-medical emission imaging. For example, the sensors are used for 2D (planar) image formation only without tomography. In other examples, the tiled sensors are used for a limited angle tomography device, multiplexed image formation for tomography, Compton camera image formation, or a hybrid Compton camera and multiplexed image formation. Any imager using a gamma camera may benefit from efficiently filling available space with room temperature semiconductor detectors enabling 2D tiling or 3D stacking and/or tiling. Some simple (e.g., hexagonal tiling within a rectangle with integer scaling) are provided herein, but lattice constraints do not have to be fulfilled (e.g., accommodate quasi lattices).

Figure 1:
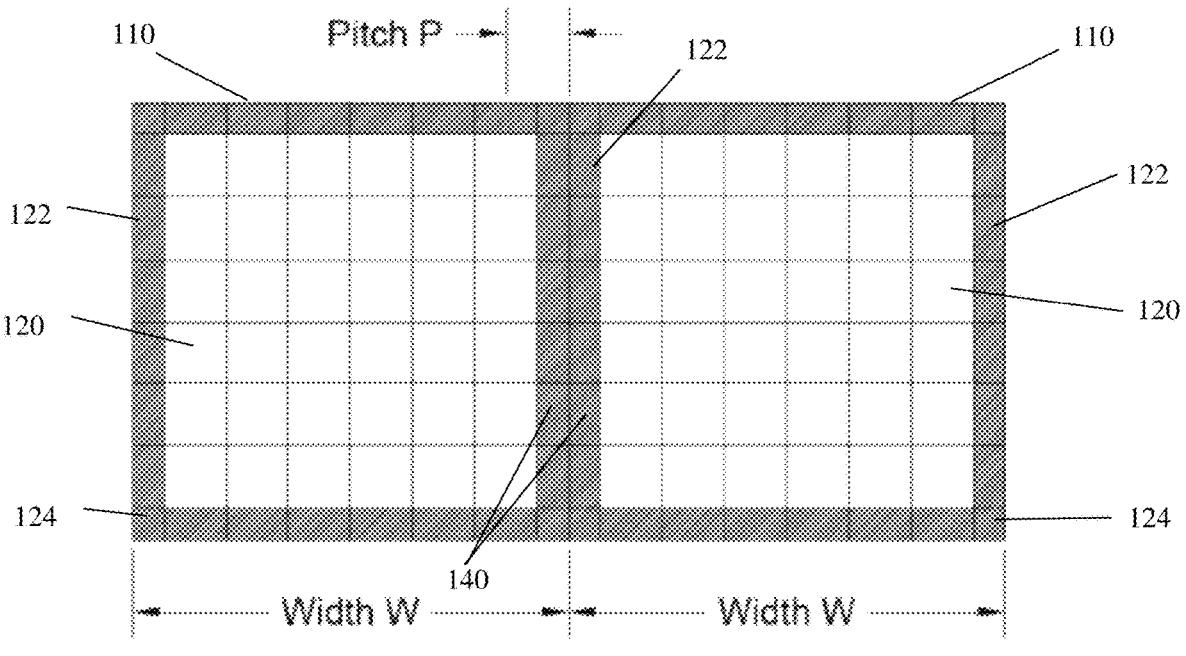
FIG. 1 illustrates one embodiment of a tiled arrangement of detectors with a square grid.
Figure 2:
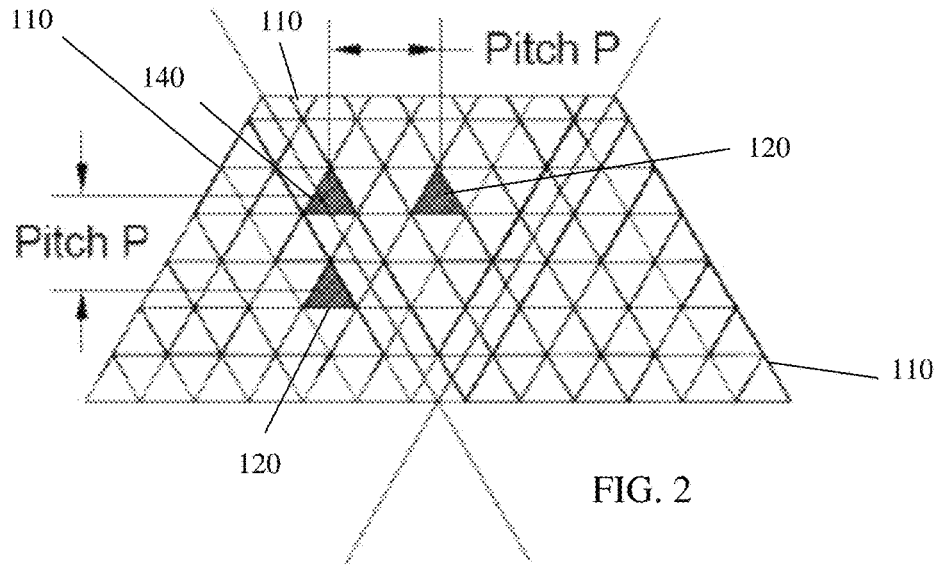
FIG. 2 illustrates another embodiment of a tiled arrangement of detectors with a triangular grid.
Figure 3:
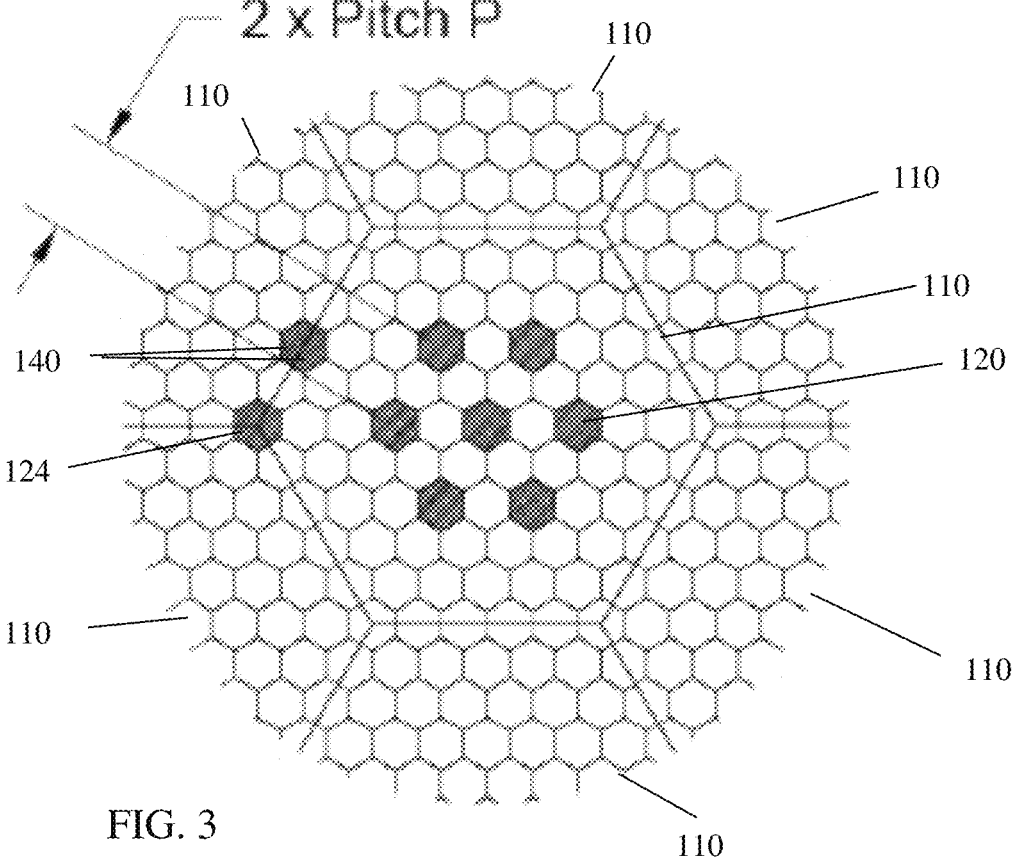
FIG. 3 illustrates yet another embodiment of a tiled arrangement of detectors with a hexagonal grid.

FIG. 1 shows one embodiment of a detector system (e.g., SPECT detector system) with tiled detectors 110. FIGS. 2 and 3 show other embodiments of the detector system with tiled detectors 110. A solid-state sensor is formed from multiple detectors 110. One or more of the detectors 110 has edge pixels 122 sized and shaped to improve performance when tiled adjacent other detectors 110. In alternative embodiments, only one detector is used. The benefits of the reduced size edge electrodes may be provided for even a single detector or tile in a module.

The detector system as shown in FIG. 1 includes two detectors 110 in a tiled arrangement. Additional detectors 110 may be tiled, such as three, four, or more detectors 110 tiled in a linear, square, "L," "T," or another pattern. FIG. 1 shows two detectors 110 tiled in a linear pattern. FIG. 2 shows three detectors 110 tiled in a linear pattern. FIG. 3 shows seven detectors 110 tiled in a "flower" pattern.

This arrangement of detectors 110 may be positioned in a frame, mounted to a carrier, and/or held between plates. Additional, different, or fewer components may be provided, such as including a collimator (e.g., multi-channel collimator) and/or application specific integrated circuits for detection electronics.

The detector 110 is a semiconductor, such as a semiconductor wafer as a room temperature semiconductor detector. The detector 110 is a solid-state detector. Any material may be used, such as SI, CZT, CdTe, and/or other material. The detector 110 is created with wafer fabrication at any thickness, such as about 4 mm for CZT. Any size may be used, such as about 5×5 cm.

The detector 110 is designed and configured to detect gamma emissions, such as emissions from a patient. For example, the semiconductor is formed as an array of silicon photon multiplier cells where anode electrodes define the detector cells.

The detectors 110 are square or have a square shape for the emission detection face. Other shapes than square may be used, such as triangular (see FIG. 2) or hexagonal (see FIG. 3). The semiconductor wafer has a square or other shape of the detection face (plane for receiving emissions). In the embodiments of FIGS. 1-3, each interior detection cell 120 (shown white without shading) and corresponding anode electrode have the same shape (e.g., square (FIG. 1), triangular (FIG. 2), or hexagonal (FIG. 3) as the detector 110.

The different detectors 110 of the tiled arrangement have the same size, shape, and pixel grid pattern. In other embodiments, one or more detectors 110 of the tiled arrangement have different size, shape, and/or pixel grid pattern.

The detector 110 is a pixelated detector or has pixelated detector cells. The detector 110 forms an array of sensors or pixelated detector cells 120, 122, 124. For example, the 2.5×2.5 cm or 5×5 cm detector 110 is a 11×11 or 21×21 pixel array of interior detection cells 120 with a pixel pitch of about 2.2 mm. Each detection cell 120, 122, 124 of the array may separately detect an emission event. Other numbers of pixels, pixel pitch, and/or size of arrays may be used. Other grids than rectangular may be used, such as a triangular distribution (see FIG. 2) or hexagonal distribution (see FIG. 3) of pixels or interior detection cells 120.

Anode and cathode electrodes are provided on opposite surfaces of the detector 110. In the example herein, the lower voltage (e.g., 10 volts or less) anode electrodes are shown and define the detection cells 120, 122, 124. The anode electrodes are conductors (e.g., conductive pads or traces) exposed on a surface of the detector 110. The electrodes have a same pitch as the detection cells 120, 122, 124 and are electrically isolated from each other for separate electrical connections to the detection cells 120, 122, 124 of the detector 110.

The interior detector cells 120 have a same shape as the detectors 110 of which they are part. For example, the interior detection cells 120 of FIG. 1 are square, of FIG. 2 are triangular, and of FIG. 3 are hexagonal. In alternative embodiments, one or more interior detector cells 120 have a different shape than the detector 110. All the interior detector cells 120 have a same shape, but a variety of shapes in a given detector 110 may be used.

One or more edges, such as all four edges of the square detectors 110 of FIG. 1, have edge detector cells 122, 124 with a different size and/or shape than the interior detector cells 120. Anodes of a single layer of the array (e.g., column or row) in the plane of the detection face on each edge have different size and/or shape than the anodes of the interior. The anodes of one or more edges are optimized by size and/or shape for tiling with other detectors 110.

Rather than all the pixels or detector cells 120, 122, 124 having a same size and/or shape, the edge or corner pixels or detector cells 122, 124 on the edges of the detector have a smaller size and/or different shape than the interior detector cells 120.

Interior detector cells 120 have the desired pitch P in the desired grid pattern. The edge detector cells 122 have a lesser area than the interior detector cells 120. For tiling, the edge detector cells 122 are sized to combine in pairs across the detectors 110, forming a combined cell 140 of two edge detector cells 122 from different detectors 110. To maintain the pitch, P, the edge detector cells 122 of each detector 110 are less than the area of the interior detectors 120 so that the combination cell 140 has a same area and/or distance across as the interior detectors 120.

The edge detector cells 122 to be paired for forming a combined cell 140 have a substantially equal area. Substantially is used to allow for manufacturing tolerance. In alternative embodiments, the edge detector cells 122 of one detector 110 are larger than the edge detector cells 122 of another detector 110, such as shown in FIG. 2.

The edge detector cells 122 have a same or different shape than the interior detector cells 120. Since the edge detector cells 122 are about half or less of the interior detector cells 120, the edge detector cells 122 have half or less of the shape of the interior detector cells 120. In the example of FIG. 1, the edge detector cells 122 are rectangles with two sides a same length as the interior detector cells 120 and half or less of the width of the interior detector cells 120. In the example of FIG. 2, some of the edge detector cells 122 are triangles, such as by the top part of a full triangle of the interior detector cells 120 being separated. Some of the edge detector cells 122 are trapezoids, such as the remaining part of the full triangle of the interior detector cells 120 after the top triangular part is cut off. Due to the difference in shape, the area of some edge detector cells 122 (e.g., the trapezoids) may be greater than 50%. In the example of FIG. 3, the edge detector cells 122 are five sided, such as from cutting a hexagon of the interior detector cells 120 in half.

For outside corners or ends of the edges of the detectors 110, the corner detection cells 124 may have a different size and/or shape. Due to tiling, the corner detection cells 124 may form a combined cell 140 for pitch purposes with corner detection cells 124 of three or more tiled detectors 110. To maintain the pitch, the corner detection cells 124 have smaller area and/or different shape. For example, the corner detection cells 124 of FIG. 1 are square instead of rectangular. As another example, the corner detection cells 124 of FIG. 2 are triangular. In another example, the corner detection cells 124 of FIG. 3 are five sided but with a different shape than the edge detection cells 122.

The size and/or shape of the edge detector cells 122 and corner detection cells 124 are designed to maintain the pitch P, which also reduces size of pixels at the edges. The size and shape are provided to form combination cells 140 sized and shaped like or the same as the interior detector cells 120 so that a pitch of the pixelated detectors cells 120, 140 across the SPECT detectors 110 is constant. The pitch is the same across the tiled arrangement when the detectors 110 are placed adjacent to each other (e.g., edge to edge). The edge and corner detection cells 122, 124 of abutting semiconductor wafers are shaped and/or sized so that pairs (triplets or more for corner) on the edges forming the combination cells 140 have the size and shape of the interior detector cells 120. This fixes the pitch of the cells across the tiled arrangement where the combined cells 140 (i.e., combined edge detector cells 122 or combined corner detector cells 124) act as a cell for the pitch. The combined cells 140 are square (e.g., FIG. 1), triangular (e.g., FIG. 2), or hexagonal (e.g., FIG. 3).

The combination cells 140 may have the different parts (e.g., component edge detector cells 122) operate independently. The electrical or signal processing is separate for the component parts, at least for part of the signal chain. The combination provides the physical pitch. Electrically, separate signal processing is provided, at least in part, for the component cells 122, 124. The signals from the edge and corner detector cells 122, 124 of a combination cell 140 may be later combined, such as averaged or summed. In alternative embodiments, wires or other conductors are used to electrically or conductively combine the component parts as tiled, allowing the combined cell 140 to operate as a full or interior detector cell 120.

In the example of FIG. 1, two side-by-side sensors or detectors 110 have edge pixels with 50% the area of inner pixels and corner pixels with 25% of the area of inner pixels. The gap between sensors or detectors 110 is substantially zero (substantially is used for manufacturing tolerance). In the example of FIG. 2, three side-by-side sensors or detectors 110 have edge pixels with 33% (triangular edge detector cell 122) and 67% (trapezoidal edge detector cell 122) of the area of inner pixels where the gap is substantially zero. In the example of FIG. 3, seven side-by-side sensors or detectors 110 have edge pixels with 50% of the area of inner pixels where the gap is substantially zero.

Figure 4:
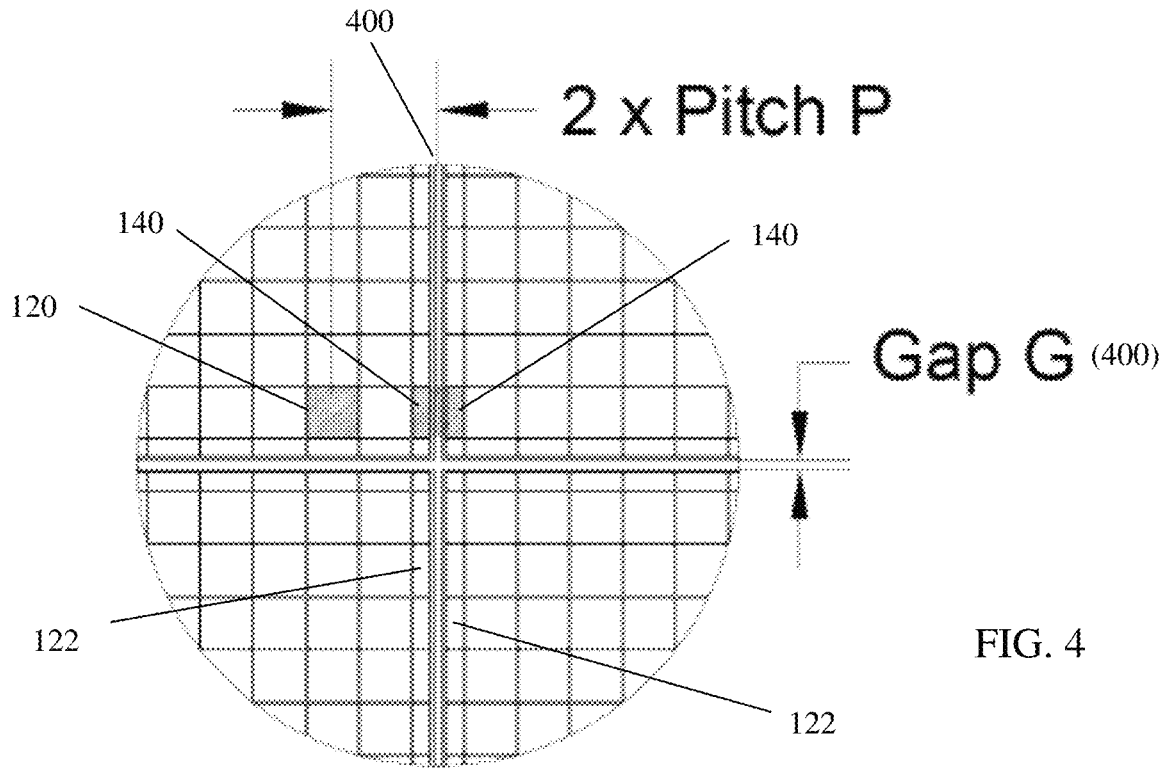
FIG. 4 illustrates a partial view of an example tiled arrangement with a gap between detectors in a square grid.
Figure 5:
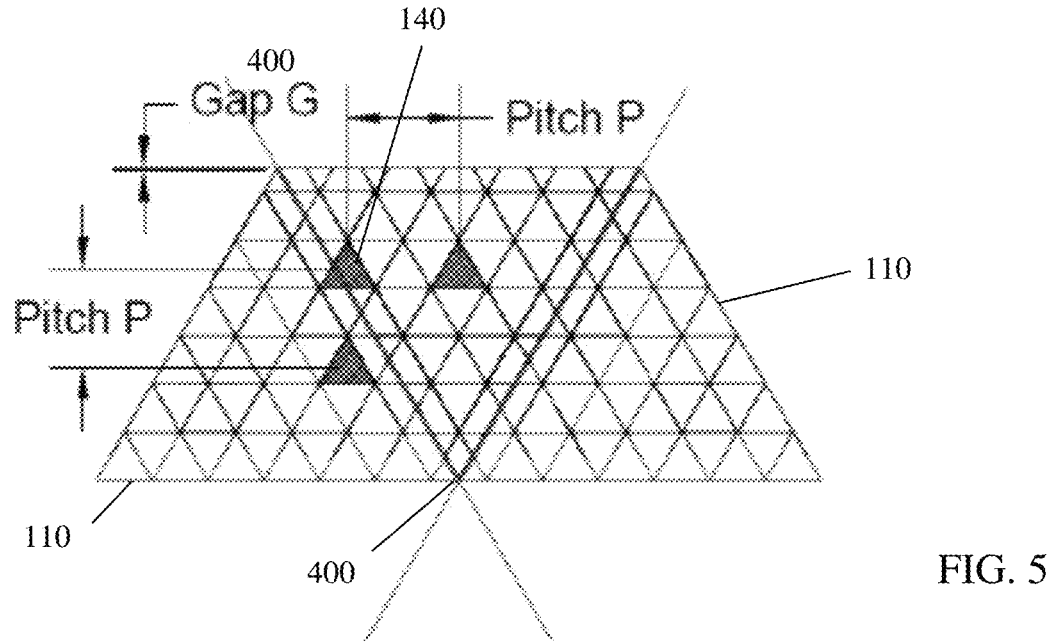
FIG. 5 illustrates the tiled arrangement of FIG. 2 with gaps between detectors.
Figure 6:
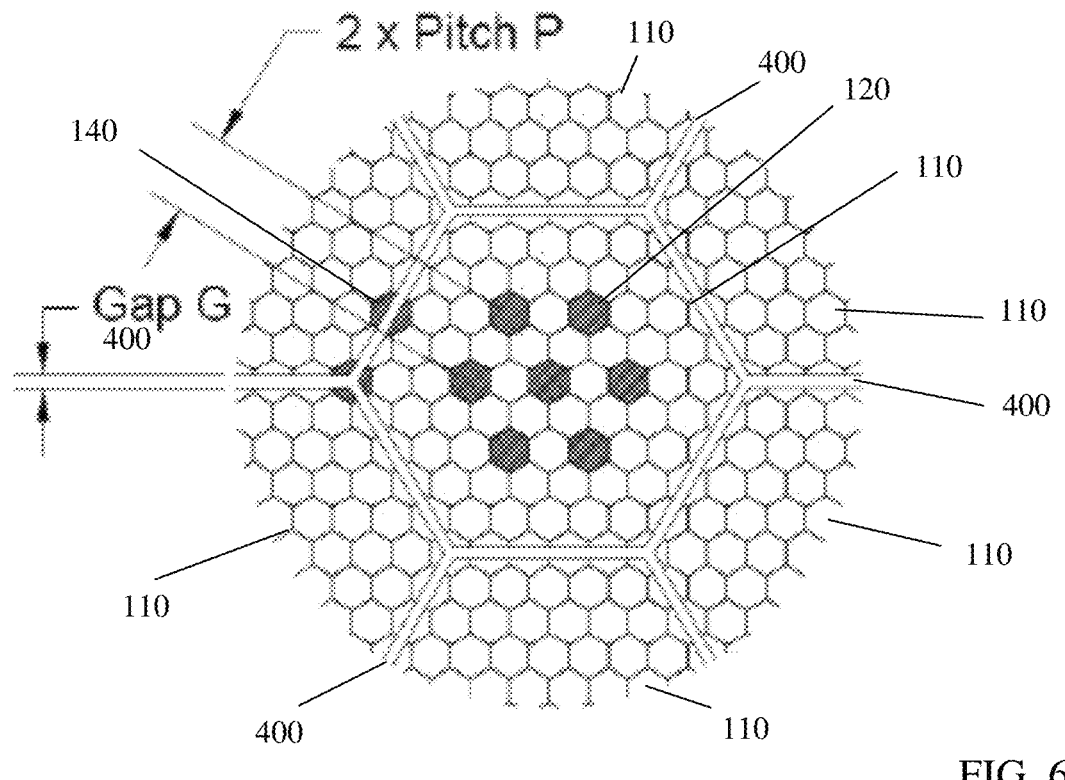
FIG. 6 illustrates the tiled arrangement of FIG. 3 with gaps between detectors.

FIGS. 4-6 show the examples of FIGS. 1-3, respectively, but with one or more added gaps 400. The gap 400 is between edges of corresponding detectors 110. The gap 400 may be greater than zero but less than the pitch P. In the examples of FIGS. 4 and 6, the gap 400 has a width of about 33% of the pitch P. In the example of FIG. 5, the gap is about 5% or 10%. Other gap widths may be used.

To account for the gap 400, the edge detector cells 122 have less than ½ the area of the interior detector cells 120. To maintain the pitch across or between detectors 110, the area is less than ½ an area of the detection cells 120 not one the edges. The corner detector cells 124 may similarly have lesser area. Increasing the gap will reduce further the relative areas of edge and corner pixels with respect to the inner pixels. In FIG. 4, four side-by-side sensors have edge pixels with less than 50% of the area of inner pixels due to additional space, the gap G (400), between sensors to maintain the same pixel Pitch P across multiple neighbor sensors. In FIG. 5, the area of the edge pixels may be less than 33% and 67% of the area of inner pixels due to additional space between sensors caused by the gap 400 while maintaining the same pixel Pitch P across multiple neighbor sensors. The trapezoidal edge detector cells 122 may have greater area than 50% even with the gap 400. In FIG. 6, the area of inner pixels is less than 50% of the area of the interior pixels due to the gap 400 while maintaining the same pixel Pitch P across multiple neighbor sensors.

The detectors or tiles may have any symmetry. The electrode pattern and the crystal pattern can be of different space groups. Assembly may yield one module, which can be used to tile into a detector head. The module uses a symmetry pattern that is most optimal between commercial needs and performance needs. Any tiling whereby the modules have different operations on the unit cell not completely covering the module cell there is need for edge tiling. If the unit cell is just scaled to achieve the module unit cell, and the scaling is not an integer, then edge tiling is used. In general symmetry operations of translation, rotation about an axis yields a 2d tiling of space or lattice. Repeating patterns in 2D have 1, 2, 3, 4, or 6 fold symmetry, and cannot have 5 or 7-fold symmetry (360/n; n=1,2,3,4,6). Quasi crystals have 5 or 7 fold symmetry and are included here as they can also form a quasi lattice. While there are 17 space groups (rotation (5); rotation and reflection (5); reflection (7)) in 2D there are only 5 basic lattice types. Thus if the detector module is of one type, yet the element of another then edge tiling is used. The tiling with the module is one aspect and tiling within a module the other.

Figure 7:
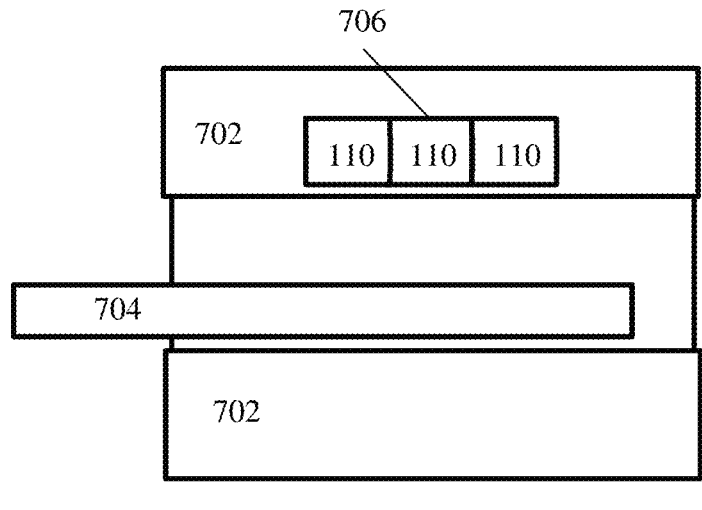
FIG. 7 is cross-section view of an imager or system.

FIG. 7 shows the detector system used in a medical system or imager (e.g., a SPECT detector system). The detector system is used as a gamma camera 706 or part of the gamma camera 706 in the system.

The system is an imaging system for imaging a patient on the bed 704. The gamma camera 706 formed by the detector system (e.g., tiled detectors 110) detects emissions from the patient.

The system 700 includes a housing 702. The housing 702 is metal, plastic, fiberglass, carbon (e.g., carbon fiber), and/or other material. In one embodiment, different parts of the housing 702 are of different materials.

The housing 702 forms a patient region (e.g., bore) into which the patient is positioned for imaging. The bed 704 may move the patient within the patient region to scan different parts of the patient at different times. Alternatively, or additionally, a gantry holding the detector system moves the detectors 110.

The gamma camera 706 is adjacent the patient region, such as mounted to a moveable gantry. The gamma camera 706 includes two or more semiconductor detectors 110, such as pixelated detectors with detection cells, in a tiled arrangement. By tiling detectors 110 adjacent to each other with or without gap, a larger field of view gamma camera is provided. By including edge and corner detector cells sized and shaped to maintain pitch across the detectors 110 as tiled with or without a gap, better spectral performance is provided.

Figure 8:
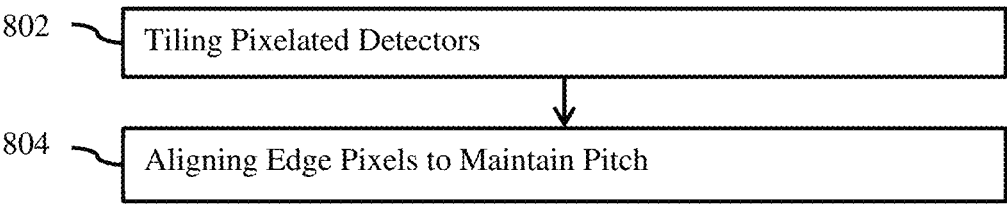
FIG. 8 is a flow chart diagram of an example embodiment of a method for forming a gamma camera from multiple semiconductor detectors.

FIG. 8 shows one embodiment of a flow chart of a method for forming a gamma camera. By sizing edge pixels for combination, the pitch across solid-state detectors may be constant.

The method is implemented by wafer processing and/or other manufacturing. A pick-n-place machine may align and tile.

The acts are performed in the order shown (i.e., top-to-bottom or numerically) or another order (e.g., reverse). In one embodiment, act 804 is performed as part of performance of act 802.

Additional, different, or fewer acts may be provided. For example, an act for wafer fabricating the solid-state detectors is provided. The wafer fabrication may include deposition and/or etching acts to form the electrodes defining electrically independent detection cells or pixels. As another example, acts for electrically connecting to application specific integrated circuits, incorporating into a camera housing, and mounting to a gantry of a SPECT imager are provided.

In act 802, multiple solid-state detectors are tiled. The detectors are placed adjacent each other, such as placing in a frame or holder. The detectors are placed adjacent to each other, edge-to-edge, so that the emission detection faces form a larger area or face for emission detection. The detectors are square, triangular, hexagonal, or another shape. By tiling, a larger area of any shape is formed.

The detectors are tiled to have a same pitch of pixels across the tiled detectors. The tiling may include a gap or not.

In act 804, the solid-state detectors are aligned as part of the tiling. Using a frame, pins, grooves, and/or another alignment mechanism, the detectors are aligned. The relative orientation of each detector relative to one or more other detectors is established.

The alignment pairs pixels on the edges of different detectors. The pairing creates combination pixels having a same size and/or shape as pixels not on the edges of the detectors. The paired pixels, when aligned, provide the same pitch as each of the interior pixels.

In one embodiment, the edge pixels are rectangular and each have ½ or less of the area of the pixels not on the edge. In other embodiments, the edge pixels are five sided, such as ½ or less area of a hexagonal shape of pixels not on the edge.

The edge pixels are aligned to be side-by-side so that the paired pixels on the edge provide the pitch. The alignment may account for a gap, so that the aligned pixels plus part of the gap provide the pitch. The alignment results in the paired pixels having a same shape and/or size as the pixels not on the edges and/or a same shape as the detectors. The alignment may align three or more corner pixels to form a same shape and/or size as the pixels not on the edges.

The regular pitch may improve spectral performance of the detectors at the edges. The regular pitch may allow for better alignment with a multi-channel collimator.

While the invention has been described above by reference to various embodiments, many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A detector system comprising:
a first detector having a plurality of first pixelated detector cells including first interior detector cells and first edge detector cells on a first edge of the first detector; and
a second detector having a plurality of second pixelated detector cells including second interior detector cells and second edge detector cells on a second edge of the second detector;
wherein the first detector is tiled with the second detector such that the second detector is positioned adjacent to the first detector where the first edge is by the second edge;
wherein the first edge detector cells have a first lesser area than the first interior detector cells, the second edge detector cells have a second lesser area than the second interior detector cells; and
wherein the first and second lesser areas are sized such that a pair of an abutting first edge detector cell and an abutting second edge detector cell combine to form a combination cell having substantially the same area and shape as one of the first interior detector cells so that a pitch of the first and second pixelated detectors cells across the first and second detectors is constant.

2. The detector system of claim 1 wherein the first and second interior detector cells and the combination cells are square, the first and second edge detector cells being rectangular.

3. The detector system of claim 1 wherein the first and second interior detector cells and the combination cells are triangular, some of the first and second edge detector cells being triangular and others of the first and second edge detector cells being trapezoidal.

4. The detector system of claim 1 wherein the first and second interior detector cells and the combination cells are hexagonal, the first and second edge detector cells being five sided.

5. The detector system of claim 1 wherein the first and second lesser areas are substantially equal.

6. The detector system of claim 1 wherein the first and second lesser areas are about ½ of areas of the first and second interior detector cells, respectively.

7. The detector system of claim 1 further comprising a gap less than the pitch between the first and second detectors, wherein the first and second lesser areas are less than ½ of areas of the first and second interior detector cells, respectively, such that the pitch is constant.

8. The detector system of claim 1 wherein the first and second detectors comprise room temperature semiconductor detectors.

9. The detector system of claim 1 wherein the first and second detectors have a same shape, and wherein the first and second interior detector cells have the same shape.

10. The detector system of claim 1 wherein the first and second pixelated detector cells include corner edge detector cells being ½ or less of the first and second lesser areas.

* * * * *